US011890070B2

(12) United States Patent
Lambrecht et al.

(10) Patent No.: US 11,890,070 B2
(45) Date of Patent: Feb. 6, 2024

(54) INSTRUMENT RELEASE

(71) Applicant: Intuitive Surgical Operations, Inc., Sunnyvale, CA (US)

(72) Inventors: Bram Gilbert Antoon Lambrecht, Sunnyvale, CA (US); Robert E. Holop, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1337 days.

(21) Appl. No.: 16/317,243

(22) PCT Filed: Mar. 29, 2017

(86) PCT No.: PCT/US2017/024687
§ 371 (c)(1),
(2) Date: Jan. 11, 2019

(87) PCT Pub. No.: WO2018/013187
PCT Pub. Date: Jan. 18, 2018

(65) Prior Publication Data
US 2019/0254763 A1    Aug. 22, 2019

Related U.S. Application Data

(60) Provisional application No. 62/362,454, filed on Jul. 14, 2016.

(51) Int. Cl.
*A61B 34/35*      (2016.01)
*A61B 46/10*      (2016.01)
(Continued)

(52) U.S. Cl.
CPC ............. *A61B 34/35* (2016.02); *A61B 34/30* (2016.02); *A61B 46/10* (2016.02); *A61B 90/57* (2016.02);
(Continued)

(58) Field of Classification Search
CPC .......... A61B 2017/00477; A61B 34/30; A61B 46/10; Y10T 403/59; Y10T 403/595
See application file for complete search history.

(56) References Cited

U.S. PATENT DOCUMENTS

| 793,510 A | 6/1905 | Cramer et al. |
| 4,117,359 A | 9/1978 | Wehde |

(Continued)

FOREIGN PATENT DOCUMENTS

| CN | 2573759 Y | 9/2003 |
| JP | H06114000 A | 4/1994 |

(Continued)

OTHER PUBLICATIONS

Extended European Search Report for Application No. EP19195298.5 dated Nov. 12, 2019, 10 pages (ISRG04151D1/EP).

(Continued)

*Primary Examiner* — Daniel J Wiley

(57) ABSTRACT

A medical instrument includes a backend and a pair of release elements. The backend includes a docking feature shaped to engage a docking structure such as a docking port of a surgical robot or a sterile adaptor for a surgical robot. Each release element is coupled to the backend and may include an activation feature on one side of the backend and a push tab extending from either an opposite side or the same side of the backend. Movement of the activation features moves the push tabs from being aligned with the docking feature to pushing on the docking structure, permitting the medical instrument to be disengaged from the docking structure. Optionally, a coupling of the release elements limits a movement of the activation features.

20 Claims, 10 Drawing Sheets

(51) Int. Cl.
  *A61B 90/57* (2016.01)
  *A61B 34/30* (2016.01)
  *A61B 17/00* (2006.01)
(52) U.S. Cl.
  CPC ... *A61B 2017/00477* (2013.01); *Y10T 403/59* (2015.01); *Y10T 403/595* (2015.01)

(56) References Cited

U.S. PATENT DOCUMENTS

| | | | |
|---|---|---|---|
| 4,259,876 A | 4/1981 | Belyanin et al. | |
| 4,281,447 A | 8/1981 | Miller et al. | |
| 4,283,165 A | 8/1981 | Vertut | |
| 4,341,144 A | 7/1982 | Milne et al. | |
| 4,696,524 A | 9/1987 | Cloyd | |
| 4,899,608 A | 2/1990 | Knappe et al. | |
| 5,441,042 A | 8/1995 | Putman et al. | |
| 5,674,024 A | 10/1997 | Daumal et al. | |
| 5,792,135 A | 8/1998 | Madhani et al. | |
| 6,007,550 A | 12/1999 | Wang et al. | |
| 6,331,181 B1 | 12/2001 | Tierney et al. | |
| 6,371,952 B1 | 4/2002 | Madhani et al. | |
| 6,394,998 B1 | 5/2002 | Wallace et al. | |
| 6,459,926 B1 | 10/2002 | Nowlin et al. | |
| 6,494,662 B1 | 12/2002 | De | |
| 6,817,974 B2 | 11/2004 | Cooper et al. | |
| 6,994,708 B2 | 2/2006 | Manzo et al. | |
| 7,261,726 B2 | 8/2007 | Jinno et al. | |
| 7,331,967 B2 | 2/2008 | Lee et al. | |
| 7,524,320 B2 | 4/2009 | Tierney et al. | |
| 7,666,191 B2 | 2/2010 | Orban, III et al. | |
| 7,699,855 B2 | 4/2010 | Anderson | |
| 7,727,244 B2 | 6/2010 | Orban, III et al. | |
| 7,823,330 B2 | 11/2010 | Ostrowski et al. | |
| 7,886,743 B2 | 2/2011 | Cooper et al. | |
| 7,935,130 B2 | 5/2011 | Williams et al. | |
| 7,963,913 B2 | 6/2011 | Devengenzo et al. | |
| 8,142,447 B2 | 3/2012 | Cooper et al. | |
| 8,333,755 B2 | 12/2012 | Cooper et al. | |
| 8,444,631 B2 | 5/2013 | Yeung et al. | |
| 8,479,969 B2 | 7/2013 | Shelton, IV et al. | |
| 8,506,555 B2 | 8/2013 | Ruiz et al. | |
| 8,551,115 B2 | 10/2013 | Steger et al. | |
| 8,602,031 B2 | 12/2013 | Reis et al. | |
| 8,644,988 B2 | 2/2014 | Prisco et al. | |
| 8,771,270 B2 | 7/2014 | Burbank et al. | |
| 8,800,838 B2 | 8/2014 | Shelton, IV et al. | |
| 8,911,471 B2 | 12/2014 | Spivey et al. | |
| 9,028,494 B2 | 5/2015 | Shelton, IV et al. | |
| 9,043,027 B2 | 5/2015 | Durant et al. | |
| 9,078,684 B2 | 7/2015 | Williams et al. | |
| 9,113,899 B2 * | 8/2015 | Garrison | A61B 18/1445 |
| 9,121,494 B2 | 9/2015 | Buchleitner et al. | |
| 9,198,714 B2 | 12/2015 | Worrell et al. | |
| 9,204,923 B2 | 12/2015 | Manzo et al. | |
| 9,232,979 B2 | 1/2016 | Parihar et al. | |
| 9,259,274 B2 | 2/2016 | Prisco et al. | |
| 9,291,793 B2 | 3/2016 | Cooper | |
| 9,339,342 B2 | 5/2016 | Prisco et al. | |
| 9,524,022 B2 | 12/2016 | Nakayama | |
| 9,687,312 B2 | 6/2017 | Dachs, II et al. | |
| 9,750,519 B2 * | 9/2017 | Garrison | A61B 18/1482 |
| 9,750,578 B2 | 9/2017 | Alden et al. | |
| 9,757,149 B2 | 9/2017 | Cooper et al. | |
| 9,913,694 B2 | 3/2018 | Brisson | |
| 9,993,313 B2 | 6/2018 | Schuh et al. | |
| 10,016,244 B2 | 7/2018 | Cooper et al. | |
| 10,022,193 B2 | 7/2018 | Cooper et al. | |
| 10,130,366 B2 | 11/2018 | Shelton, IV et al. | |
| 10,271,911 B2 | 4/2019 | Cooper et al. | |
| 10,420,622 B2 | 9/2019 | Dachs et al. | |
| 10,478,256 B2 | 11/2019 | Shelton, IV et al. | |
| 10,543,051 B2 | 1/2020 | Schena et al. | |
| 10,582,980 B2 | 3/2020 | Scheib et al. | |
| 10,595,836 B2 | 3/2020 | Smaby et al. | |
| 10,603,125 B2 | 3/2020 | Komuro et al. | |
| 10,624,709 B2 | 4/2020 | Remm | |
| 10,631,949 B2 | 4/2020 | Schuh et al. | |
| 10,639,119 B2 | 5/2020 | Dachs, II et al. | |
| 10,653,489 B2 | 5/2020 | Kopp | |
| 10,780,573 B2 | 9/2020 | Vaders | |
| 10,912,616 B2 | 2/2021 | Dachs, II et al. | |
| 10,932,868 B2 | 3/2021 | Solomon et al. | |
| 10,980,556 B2 | 4/2021 | Anderson et al. | |
| 11,090,124 B2 | 8/2021 | Holop et al. | |
| 2002/0087048 A1 | 7/2002 | Brock et al. | |
| 2002/0096885 A1 | 7/2002 | Gomez et al. | |
| 2002/0111635 A1 | 8/2002 | Jensen et al. | |
| 2002/0153221 A1 | 10/2002 | Schnepf | |
| 2004/0035243 A1 | 2/2004 | Duval | |
| 2005/0042943 A1 | 2/2005 | Mocivnik et al. | |
| 2005/0089345 A1 | 4/2005 | Yasumoto et al. | |
| 2005/0277875 A1 | 12/2005 | Selkee | |
| 2007/0043338 A1 | 2/2007 | Moll et al. | |
| 2007/0232858 A1 | 10/2007 | MacNamara et al. | |
| 2008/0046122 A1 | 2/2008 | Manzo et al. | |
| 2008/0065102 A1 | 3/2008 | Cooper et al. | |
| 2008/0065105 A1 | 3/2008 | Larkin et al. | |
| 2008/0087871 A1 | 4/2008 | Schena et al. | |
| 2008/0103491 A1 | 5/2008 | Omori et al. | |
| 2008/0196533 A1 | 8/2008 | Bergamasco et al. | |
| 2009/0088774 A1 | 4/2009 | Swarup et al. | |
| 2010/0011900 A1 | 1/2010 | Burbank et al. | |
| 2010/0170519 A1 | 7/2010 | Romo et al. | |
| 2010/0175701 A1 | 7/2010 | Reis et al. | |
| 2010/0318101 A1 | 12/2010 | Choi et al. | |
| 2010/0331820 A1 | 12/2010 | Prisco et al. | |
| 2011/0015650 A1 | 1/2011 | Choi et al. | |
| 2011/0118754 A1 | 5/2011 | Dachs, II et al. | |
| 2011/0160743 A1 | 6/2011 | Espinal | |
| 2011/0213383 A1 | 9/2011 | Lee et al. | |
| 2011/0277775 A1 | 11/2011 | Holop et al. | |
| 2011/0282356 A1 | 11/2011 | Solomon et al. | |
| 2011/0282357 A1 | 11/2011 | Rogers et al. | |
| 2011/0295269 A1 | 12/2011 | Swensgard et al. | |
| 2011/0295270 A1 | 12/2011 | Giordano et al. | |
| 2012/0021867 A1 | 1/2012 | Rosmarin | |
| 2012/0111136 A1 | 5/2012 | Kawakami | |
| 2012/0118917 A1 | 5/2012 | Naughton et al. | |
| 2012/0123441 A1 | 5/2012 | Au et al. | |
| 2012/0239060 A1 | 9/2012 | Orban, III et al. | |
| 2012/0245596 A1 | 9/2012 | Meenink | |
| 2012/0259337 A1 * | 10/2012 | del Rio | A61B 17/162 29/428 |
| 2012/0289974 A1 | 11/2012 | Rogers et al. | |
| 2014/0005678 A1 | 1/2014 | Shelton, IV et al. | |
| 2014/0005708 A1 | 1/2014 | Shelton, IV | |
| 2014/0100558 A1 | 4/2014 | Schmitz et al. | |
| 2014/0276723 A1 | 9/2014 | Parihar et al. | |
| 2015/0008090 A1 | 1/2015 | Adamczak et al. | |
| 2015/0150635 A1 | 6/2015 | Kilroy et al. | |
| 2015/0157355 A1 | 6/2015 | Price et al. | |
| 2016/0058443 A1 | 3/2016 | Yates et al. | |
| 2016/0151115 A1 | 6/2016 | Karguth et al. | |
| 2016/0184034 A1 | 6/2016 | Holop et al. | |
| 2016/0184036 A1 | 6/2016 | Solomon et al. | |
| 2016/0184037 A1 | 6/2016 | Cooper et al. | |
| 2016/0199138 A1 | 7/2016 | Cooper et al. | |
| 2016/0361025 A1 | 12/2016 | Dachs, II et al. | |
| 2017/0086930 A1 * | 3/2017 | Thompson | A61B 34/30 |
| 2017/0165017 A1 | 6/2017 | Chaplin et al. | |
| 2018/0055583 A1 | 3/2018 | Schuh et al. | |
| 2018/0126546 A1 * | 5/2018 | Vaders | A61B 34/37 |
| 2018/0280097 A1 | 10/2018 | Cooper et al. | |
| 2019/0021805 A1 * | 1/2019 | Roeder | A61B 90/361 |
| 2019/0099227 A1 | 4/2019 | Rockrohr | |
| 2019/0201022 A1 | 7/2019 | Schoettgen et al. | |
| 2019/0223966 A1 | 7/2019 | Holop et al. | |
| 2019/0298471 A1 | 10/2019 | Holop | |
| 2021/0186544 A1 | 6/2021 | Anderson et al. | |
| 2021/0282793 A1 | 9/2021 | Anderson et al. | |
| 2023/0210614 A1 | 7/2023 | Cooper et al. | |

(56) References Cited

U.S. PATENT DOCUMENTS

FOREIGN PATENT DOCUMENTS

| | | |
|---|---|---|
| JP | H10249777 A | 9/1998 |
| JP | 2002200091 A | 7/2002 |
| JP | 2003024336 A | 1/2003 |
| JP | 2005288590 A | 10/2005 |
| JP | 2006061364 A | 3/2006 |
| JP | 2010220955 A | 10/2010 |
| WO | WO-9729690 A1 | 8/1997 |
| WO | WO-2005039835 A1 | 5/2005 |
| WO | WO-2009123891 A1 | 10/2009 |
| WO | WO-2011037394 A2 | 3/2011 |
| WO | WO-2015023834 A1 | 2/2015 |
| WO | WO-2015142290 A1 | 9/2015 |

OTHER PUBLICATIONS

International Search Report and Written Opinion for Application No. PCT/US14/050838, dated Nov. 25, 2014, 11 pages.
International Search Report and Written Opinion for Application No. PCT/US14/50957, dated Nov. 21, 2014, 11 pages.
International Search Report and Written Opinion for Application No. PCT/US14/51001, dated Nov. 20, 2014, 11 pages.
International Search Report and Written Opinion for Application No. PCT/US14/51074, dated Nov. 20, 2014, 13 pages.
International Search Report and Written Opinion for Application No. PCT/US2012/037269, dated Sep. 19, 2012, 10 pages.
International Search Report and Written Opinion for Application No. PCT/US2014/051033, dated Nov. 19, 2014, 9 pages.
International Search Report and Written Opinion for Application No. PCT/US2014/051050, dated Nov. 25, 2014, 14 pages.
Office Action dated Dec. 26, 2014 for Japanese Application No. 20140021913 filed Feb. 7, 2008, 10 pages.
Office Action dated Sep. 30, 2015 for Japanese Application No. 20140021913 filed Feb. 7, 2008, 7 pages.
PCT/US09/55727 International Search Report and Written Opinion of the International Searching Authority, dated Feb. 3, 2010, 9 pages.
Extended European Search Report for Application No. 14836283.3, dated Sep. 4, 2017, 11 pages.
Extended European Search Report for Application No. 14836336.9, dated Jun. 16, 2017, 9 pages.
Extended European Search Report for Application No. 14836512.5, dated Aug. 3, 2017, 13 pages.
Extended European Search Report for Application No. 14836696.6, dated Jun. 16, 2017, 9 pages.
Office Action dated Nov. 30, 2016 for Chinese Application No. 201510185999.6 filed Sep. 2, 2009, 24 pages.
Extended European Search Report for Application No. 14836832.7, dated Jun. 9, 2017, 8 pages.
Extended European Search Report for Application No. EP14836874.9, dated Mar. 17, 2017, 10 pages.
Partial Supplementary European Search Report for Application No. EP14836283.3, dated May 17, 2017, 12 pages.
International Search Report and Written Opinion for Application No. PCT/US2017/024687, dated Jul. 5, 2017, 10 pages.
Office Action dated Jun. 22, 2017 for Japanese Application No. 2016177316 filed Sep. 12, 2016, 7 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

INSTRUMENT RELEASE

RELATED APPLICATIONS

This patent application is a U.S. national stage filing under 35 U.S.C. § 371 of International Application No. PCT/US2017/024687 (filed Mar. 29, 2017), entitled "INSTRUMENT RELEASE," which claims priority to and the benefit of the filing date of U.S. Provisional Patent Application No. 62/362,454 (filed Jul. 14, 2016), entitled "INSTRUMENT RELEASE" each of which is incorporated by reference herein in its entirety.

BACKGROUND

Some advanced robotic medical systems such as the da Vinci® Surgical System commercialized by Intuitive Surgical, Inc. employ removable medical instruments that may be mounted in docking ports on the arms of a robot. (As used herein, the terms "robot" or "robotically" and the like include teleoperation or telerobotic aspects, and teleoperated surgical systems are often referred to as "surgical robots".) Such systems generally employ a sterile barrier between the medical instruments and the robot, so that medical instruments, which come into direct contact with a patient, reside in a sterile environment on a patient side of the sterile barrier, while the robot, which never directly contacts a patient, is outside of the sterile environment. The sterile barrier typically includes a drape or sheet of plastic or other material suitable for maintaining the sterile environment, and instrument sterile adapters (ISAs) may be mounted in the sheet and positioned between the medical instruments and the robot. The ISAs typically include structures that enable medical instruments to dock with the robot and enable the robot to mechanically actuate docked medical instruments without compromising the sterile environment. A medical instrument may employ latch and release mechanisms to securely dock the medical instrument with a robot via an ISA and to release the medical instrument from the robot and the ISA, for example, when a procedure is complete.

SUMMARY

In accordance with an aspect of the invention, a medical instrument includes a backend with a pair of release levers. The backend may have a docking feature shaped to engage a docking structure such as a sterile adaptor or a docking port of a robot. Each of the release levers may be coupled to the backend and may include an activation feature (e.g., a release button) on one side of the backend and a push tab extending from an opposite side of the backend. Movement of the activation features moves the push tabs from being aligned with the docking feature to pushing on the docking structure, permitting the medical instrument to be disengaged from the docking structure.

In accordance with another disclosed aspect, a medical instrument includes a backend with a release mechanism. The backend may have a docking feature shaped to engage a docking structure. The release mechanism includes a pair of release levers and a pair of push tabs. A first release lever has an activation feature, such as a button, on one side of the backend, and a second release lever has another activation feature on an opposite side of the backend. Similarly, a first push tab of the push tabs extends from one side of the backend, and a second push tab of the push tabs extends from the other side of the backend. A coupling of the two release levers may limit a movement of the activation features. The movement of the activation features causes the push tabs to move from being aligned with the docking feature to pushing on the docking structure.

BRIEF DESCRIPTION OF THE DRAWINGS

The drawings illustrate examples for the purpose of explanation and are not of the invention itself. Use of the same reference symbols in different figures indicates similar or identical items.

DETAILED DESCRIPTION

A release mechanism for a medical instrument may push a sterile adapter retention plate away from the medical instrument using coupled levers to simultaneously press on opposite edges of the retention plate. The release mechanism particularly pushes the retention plate away symmetrically, so that the medical instrument does not get cocked to one side, which could prevent the medical instrument from sliding smoothly out of an instrument sterile adapter (ISA). The medical instrument may engage the ISA by being slid into a position at which spring action of the ISA or other docking structure may push projections on opposite sides of the medical instrument or the ISA into notches in the other of the ISA and the medical instrument. Disengaging the instrument may thus require the release mechanism to push the projections out of the notches, so that the instrument can be slid out of (or otherwise removed from) the ISA. Release buttons or other activation features of the release mechanism may be positioned on a housing of the medical instrument so that a user grasping the housing when removing the instrument can naturally activate the release mechanism and reliably push the retention plate and the instrument apart using a grasping force within desired limits.

Figure 1A:
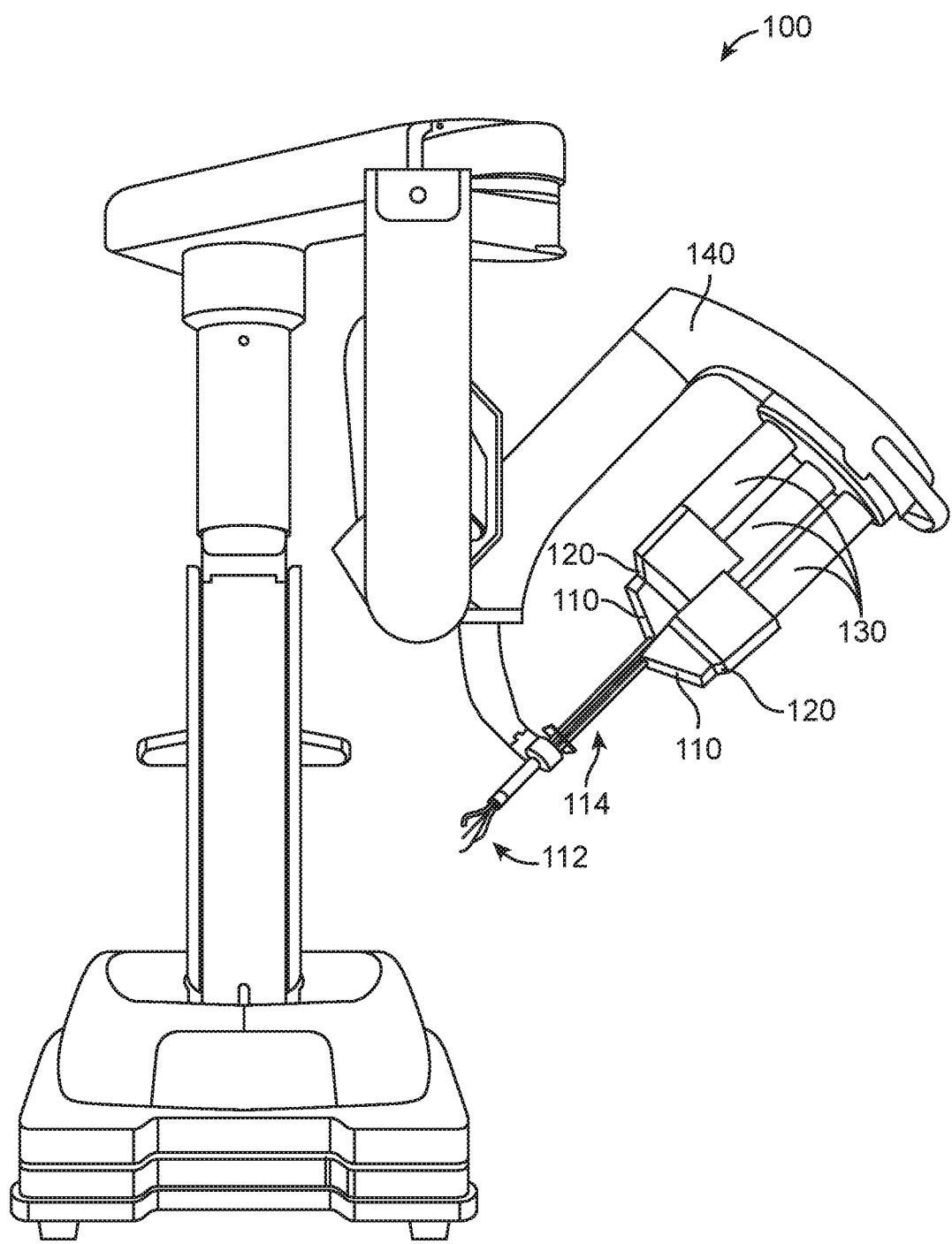
FIG. 1A shows an implementation of a medical system employing removable instruments.

FIG. 1A shows an example of a medical system 100 including replaceable medical instruments 110 that may contain release mechanisms such as disclosed herein. System 100, which may, for example, include a da Vinci® Surgical System commercialized by Intuitive Surgical, Inc., employs multiple surgical instruments 110, each of which is mounted in a docking port 120 on a manipulator arm 130 of a robot 140. A sterile barrier (not shown in FIG. 1A) including a drape and instrument adaptors may be between a patient (not shown) and robot 140. Robot 140, including manipulator arms 130 and docking ports 120, may thus be outside a sterile environment for the patient, while instruments 110 are in the sterile environment on the patient's side of the sterile barrier. Accordingly, robot 140 may not need to be sterilized for medical procedures. In contrast, instruments 110, which directly contact the patient, are compact and removable so that medical instruments 110 may be removed and sterilized or replaced between medical procedures performed using system 100. The sterile barrier may be removed from robot 140 after medical instruments 110 are remove, but the sterile barrier is typically disposed of and replaced between medical procedures.

Instruments 110 may vary in structure and purpose but may still be interchangeable, so that a user can select and mount various instruments 110 in docking ports 120 of robot 140 as needed for a particular medical procedure and can swap instruments 110 during a medical procedure to provide desired clinical functions. Each instrument 110 generally includes an end effector or distal tool 112, an instrument shaft 114, and a backend. Distal tools 112 may have different designs to implement many different functions. For example, distal tools 112 for different instruments 110 may have many different shapes or sizes and may include forceps, graspers, scalpels, scissors, cautery tools, or needle drivers to name a few possibilities. Instruments 110 having different distal tools 112 may be mounted on different arms 130 of robot 140 and may work cooperatively at the same work site. An endoscopic camera, for example, a stereoscopic camera, can also be mounted on an arm to provide visual information, particularly images of the work site in which distal tools 112 of instruments 110 may be operating.

Figure 1B:
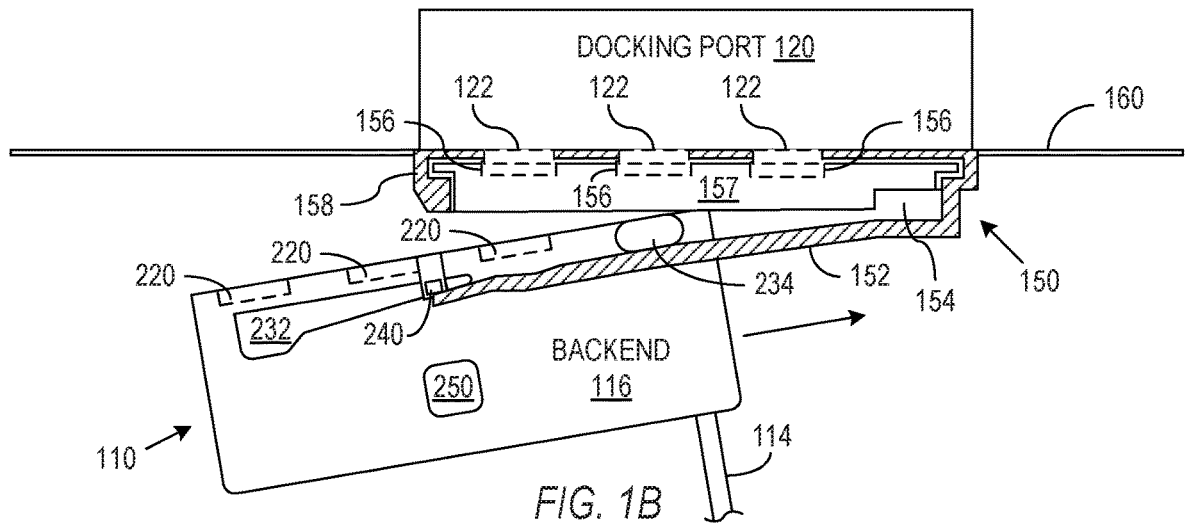
FIG. 1B shows a medical instrument being slid into a docking port of a medical system.

Docking ports 120 of robot 140 may include actuators such as drive motors that provide mechanical power to actuate mechanical structures in instruments 110 via drive couplings that connect the actuators through an ISA to inputs of instruments 110. FIG. 1B illustrates an instrument 110 beginning to engage a docking port 120. An ISA 150, which may be part of a sterile barrier, may be mounted on docking port 120 before the engagement process begins. In particular, ISA 150 may be attached to docking port 120. In the implementation shown, ISA 150 includes an outer frame 158 around a movable plate 157 containing rotatable disks 156. Outer frame 158, which is shown in cross-section to better illustrate the structure of ISA 150, may be disposed in a sheet or drape portion 160 of the sterile barrier and is sized and shape to fit docking port 120. Inner frame 157, which is sometimes referred to herein as a retention plate, may be movable relative to outer frame 158 to adjust to variability in the position of actuators in docking port 120 so that engagement features 122 of the actuators in docking port 120 may couple to disks 156 in ISA 150. In particular, springs (not shown) in the docking port 120 may provide spring loading that pushes engagement features 122 onto disks 156 and plate 157. Disks 156 in turn engage engagement features on input spindles 120 of instrument 110 when instrument 110 is fully docked.

Figure 1C:
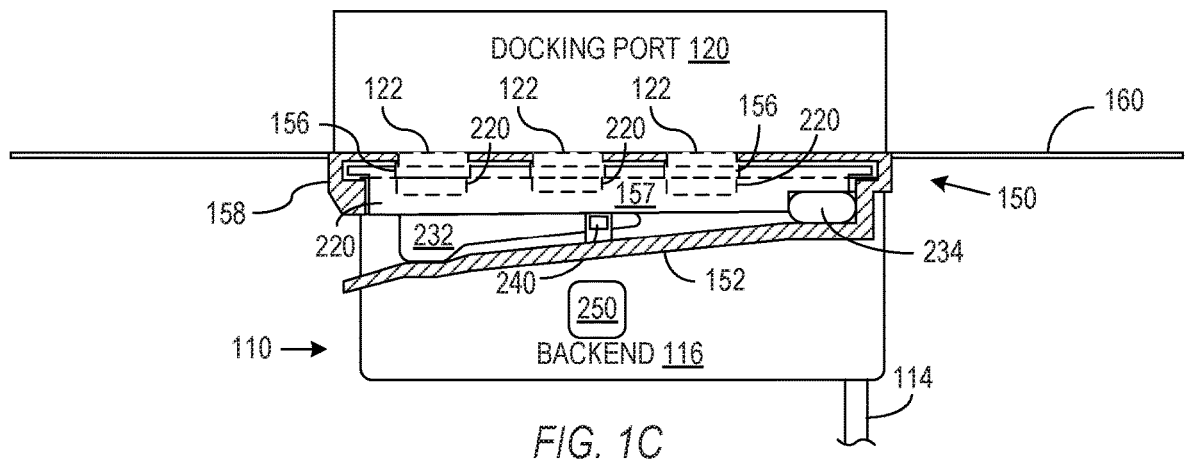
FIG. 1C shows the medical instrument in accordance with the implementation of FIG. 1B when docked in a docking port.

ISA 150 further includes rails 152 shaped to guide side rails 232 and projections 234 on opposite sides of backend 116 of instrument 110 as backend 116 is being slid into ISA 150. When projections 234 reach respective notches 154 in ISA 150, rails 152 push side rails 232 against retention plate 157 or outer frame 158 of ISA 150 and push each projection 234 into its notch 154 in ISA 150 as shown in FIG. 1C. In this docked position, engagement features 122 on drive motors in docking port 120 fit into top features of sealed disks 156 in ISA 150, and engagement features 228 on input spindles of backend 116 fit into bottom features of sealed disks 156 so that drive motors rotating engagement features 122 rotate disks 156 and input spindles 220 of instrument 110. A computer system, which may be connected to or part of the robot 140 that includes docking port 120 and which may be connected to a user interface device (not shown), may receive user commands from a surgeon or other medical personnel and may execute software that controls drive motors or other actuators in docking ports 120 as needed to rotate engagement features 122, disks 156, and input spindles 220 and thereby actuate instruments 110 according to the user commands.

Figure 1D:
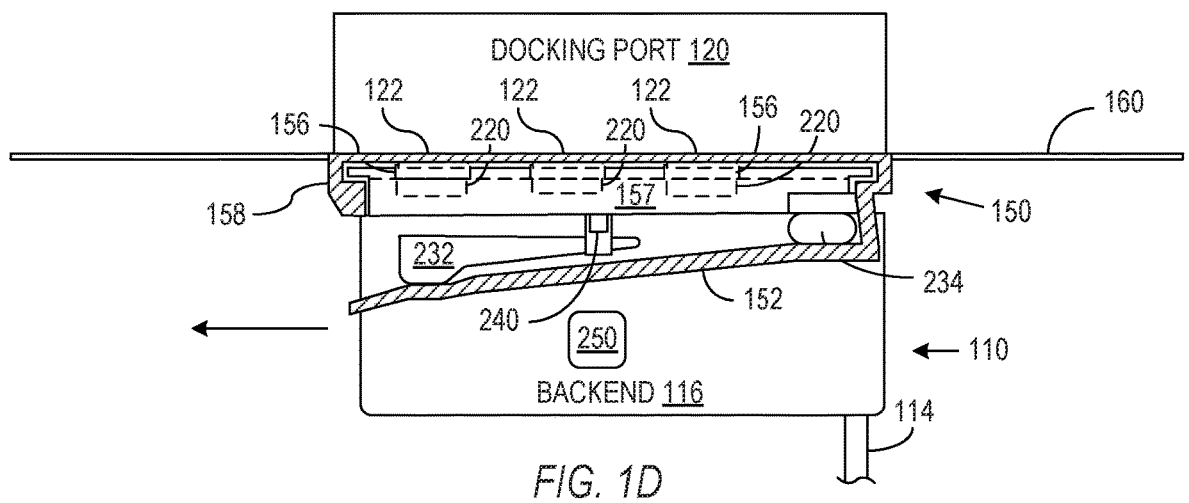
FIG. 1D shows the docked medical instrument in accordance with the implementation of FIG. 1C when a user moves or activates a release mechanism.

FIG. 1C shows the projection 234 on one side of backend 116 secured in the notch 154 on one side of ISA 150. Projections 234 and notches 154 act as lock features that prevent instrument 110 from being unintentionally removed from ISA 150. In particular, two projections 234 on opposite sides of backend 116 being pressed into notches 154 on opposite sides of ISA 150 may keep backend 116 from disengaging from docking port 120 and from sliding out of ISA 150. To release instrument 110 from docking port 120 and ISA 150, instrument 110 includes a release mechanism that includes interconnected release levers with push tabs 240 on opposite sides of backend 116. When the release mechanism is not activated, each push tab 240 may be aligned with or recessed relative to a side rail 232 so that backend 116 can slide into place and fully engage with ISA 150 and docking port 120 as shown in FIG. 1C. A user may depress release buttons 250 on opposite sides of backend 116 to activate the release mechanism and cause push tabs 240 to move up past respective rails 232 and to thereby push on ISA 150. Push tabs 240 may particularly push on plate 157, so that plate 157 moves away from backend 116 and disengages backend 116 from notches 154 and/or other engagement features of ISA 150. Push tabs 240 may also push on plate 157, so that plate 157 moves disks 156 away from backend 116 and disengages bottoms of disks 156 from input spindles 220 in backend 116. FIG. 1D shows how the action of push tabs 240 may also keep ISA 150 engaged with docking port 120 while decoupling projections 234 from notches 154 so that medical instrument 110 can be slid out of ISA 150. ISA 150 thus remains on docking port 120 when instrument 110 is released and removed.

Figure 2A:
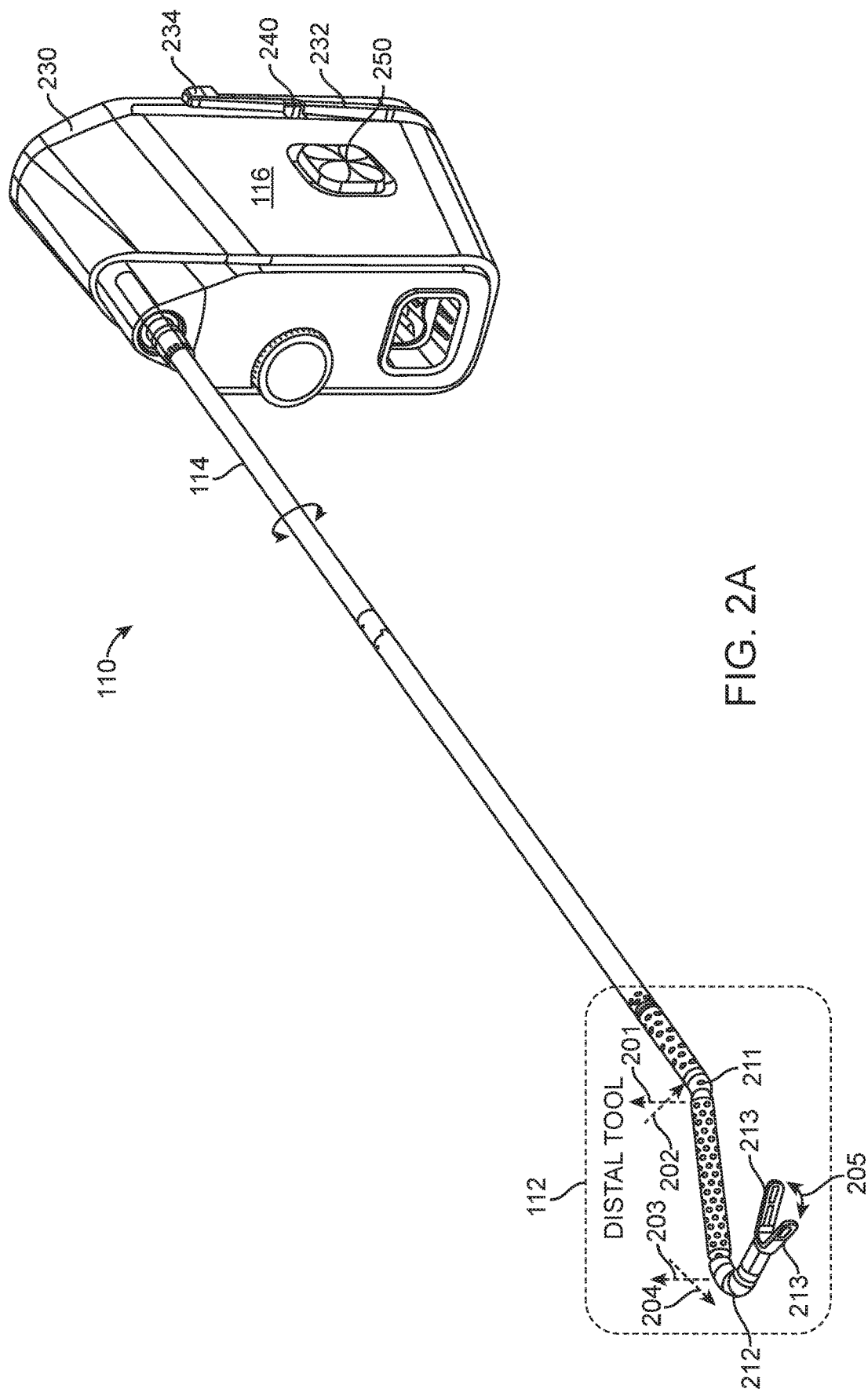
FIGS. 2A and 2B show perspective and top views of an example implementation of a medical instrument.
Figure 2B:
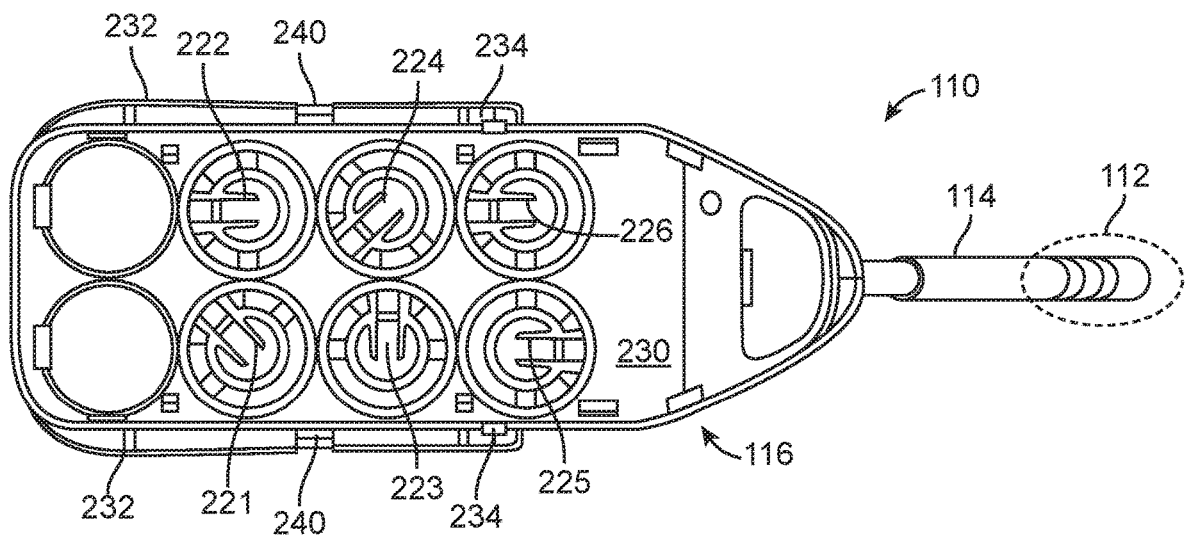

FIGS. 2A and 2B illustrate a more detailed example of an implementation of a medical instrument 110. FIG. 2A particularly shows a perspective view of an implementation having an elongated instrument shaft 114 that extends from backend 116 of instrument 110 and having a distal tool 112 at the distal end of instrument shaft 114. In the illustrated implementation, distal tool 112 has six degrees of freedom of movement relative to backend 116. Specifically, the six degrees of freedom may correspond to: pitch and yaw rotations of a portion of tool 112 about two respective perpendicular axes 201 and 202 associated with a first joint or wrist mechanism 211; pitch and yaw rotations or movement of jaws 213 relative to two respective perpendicular axes 203 and 204 associated with a second joint or wrist mechanism 212; opening or closing movement 205 of jaws 213 for "grip" actuation; and "roll" rotations of instrument shaft 114 about its central length axis 206. Other medical instruments may have more, fewer, or different degrees of freedom of movement.

Backend 116 as shown in FIG. 2B has six input spindles 221 to 226 with engagement features that are arranged in a base plate 230 and are shaped to engage actuators, e.g., engagement features of drive motors, in a docking port of a robot via an intervening ISA as illustrated in FIGS. 1B, 1C, and 1D. In general, each input spindle 221 to 226 may be part of a mechanism for actuation of a corresponding degree of freedom of movement of instrument 110. The assignment input spindles 221 to 226 to corresponding degrees of freedom must be known to the robot, so that the robot can identify and use the correct actuator or actuators to rotate the input spindle or spindles that exercise desired degree or degrees of freedom of instrument 110, but assignment of input spindles 221 to 226 to particular degrees of freedom of movement can be otherwise defined by an arbitrary standard or convention.

Base plate 230 further includes side rails 232 on opposite sides of base plate 230, and side rails 232 may be positioned and shaped for sliding of backend 116 into an ISA as illustrated in FIG. 1B. Base plate 230 may further include projections 234 that may be contiguous with respective rails 232 or separated from rails 232. Each projection 234 may be positioned and shaped to slip into a corresponding notch in the ISA so that projections 234 when in respective notches prevent backend 116 from being slid out of the ISA. Removal of the instrument may thus require lifting projections 234 out of the notches in the ISA as described above with reference to FIG. 1D.

Figure 3A:
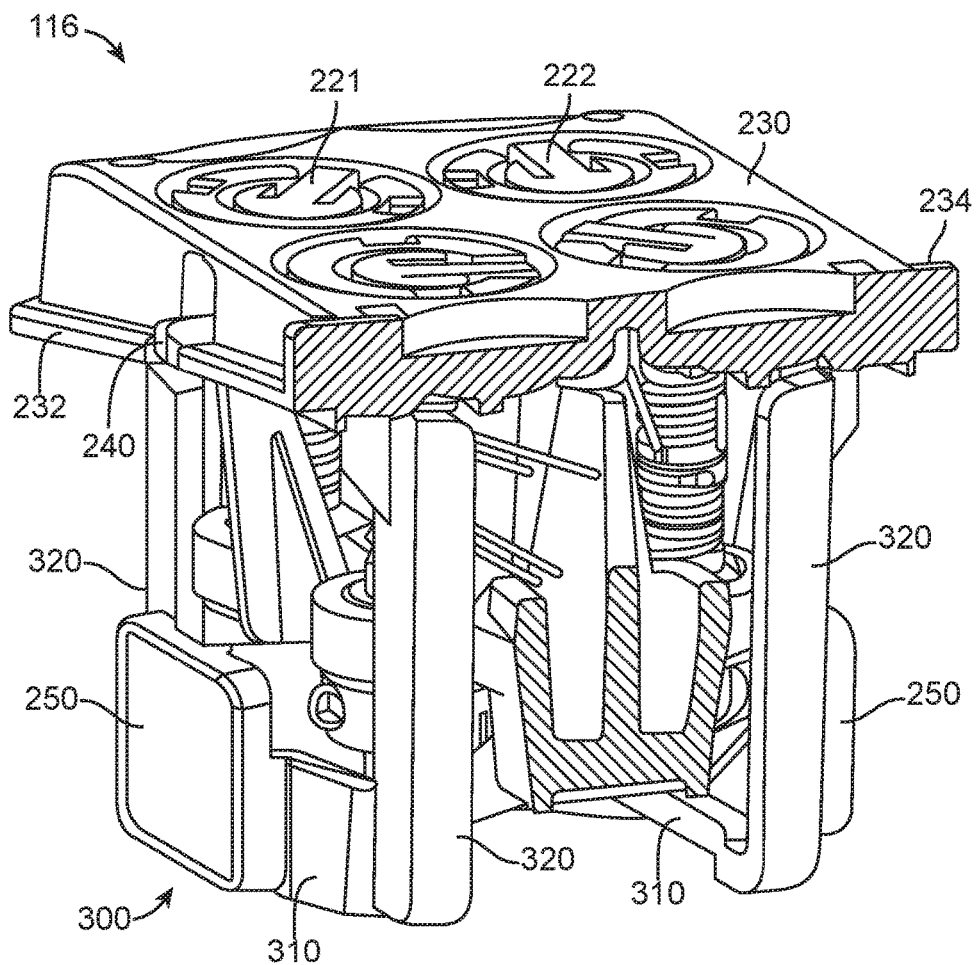
FIG. 3A shows a cut away view revealing one implementation of a release mechanism that may be inside a backend of the instrument of FIGS. 2A and 2B.
Figure 3B:
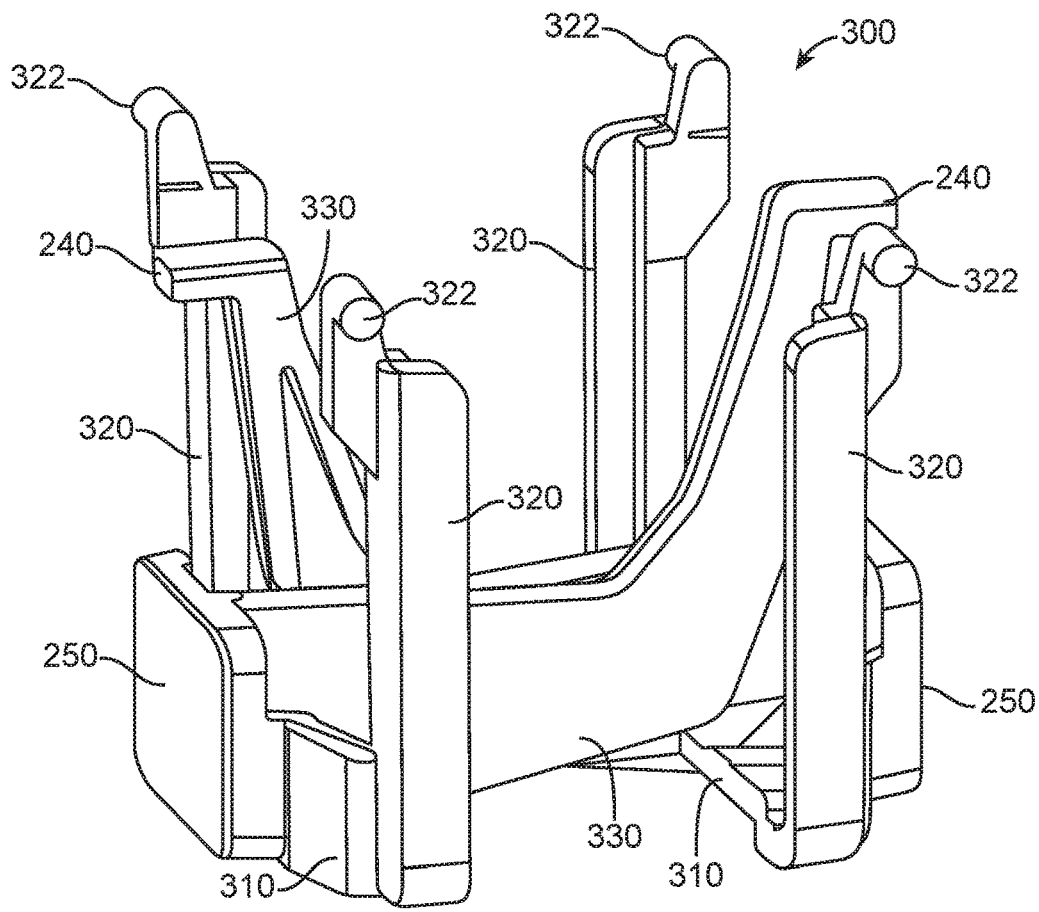
FIG. 3B shows a perspective view of the release mechanism of FIG. 3A without surrounding components in a backend of an instrument.

FIG. 3A shows a cutaway view of the instrument backend 116 of FIGS. 2A and 2B in accordance with an implementation in which a release mechanism employs a pair of identical interconnected release levers 310 that each function as a release element of a release mechanism 300. FIG. 3B shows release mechanism 300 including release levers 310 but without other structures of backend 116 that may obscure the view of the interaction of release levers 310. In release mechanism 300, each release lever 310 has a one-piece construction and may be a monolithic or molded structure that integrates and connects one push tab 240 and one release button 250. Each lever 310 further includes a pair of pivot arms 320 and a lifter arm 330. Each button 250 is couples to a crossbar extending between a pair of pivot arms 320. The two pivot arms 320 on each release lever 310 have pivots 322 (which can be implemented as axles) that extend along a desired rotation axis of the release lever 310. In backend 116 of FIG. 3A, pivots 322 of a release lever 310 rotatably attach the release lever 310 to base plate 230. Pivot arms 320 and buttons 250 may particularly be positioned toward outer edges of backend 116, so that actuation mechanisms such as input spindles 221 to 224 can occupy the central portion of backend 116 as shown in FIG. 3A. The lifter arm 330 of each release lever 310 may extend from the release button 250 of the release lever 310, between the input spindles of backend 116, across backend 116, and upward so that the push tab 240 at the end of lifter arm 330 extends from a side of backend 116 that is opposite the side on which the button 250 resides. Accordingly, a user pushing on a button 250 on one side of backend 116 causes release lever 310 to rotate and the push tab 240 on the opposite side of backend 116 to move.

Figure 4A:
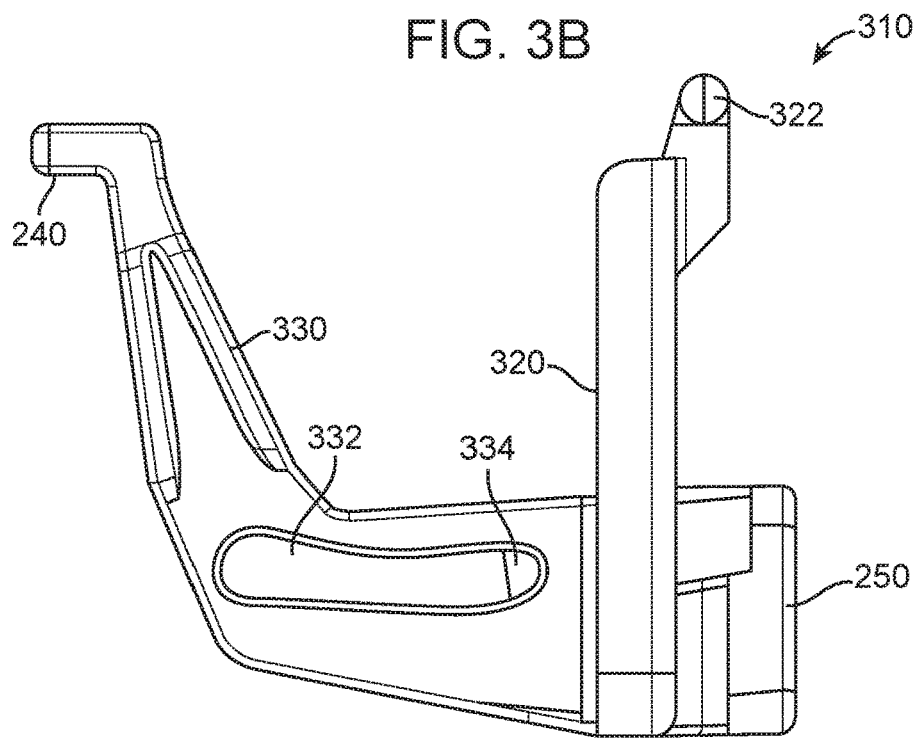
FIGS. 4A, 4B, and 4C respectively show front, side, and perspective views of one implementation of a release lever.
Figure 4B:
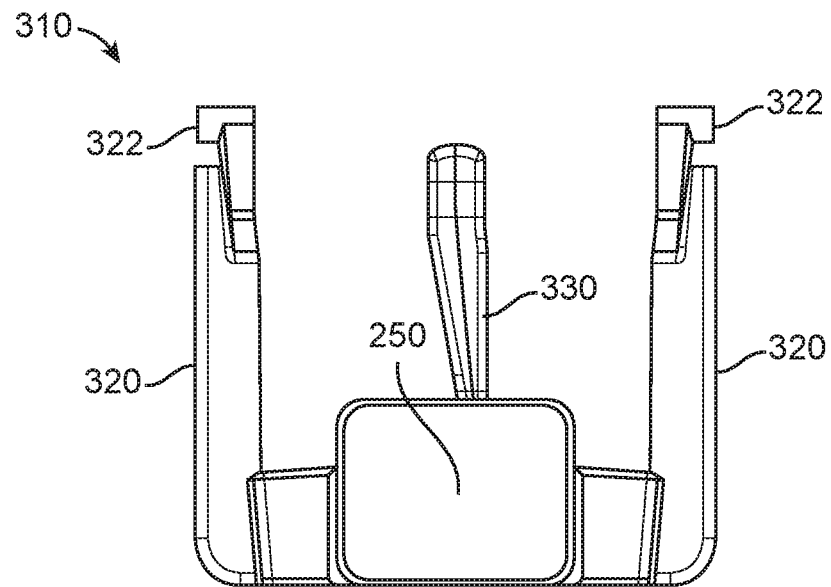
Figure 4C:
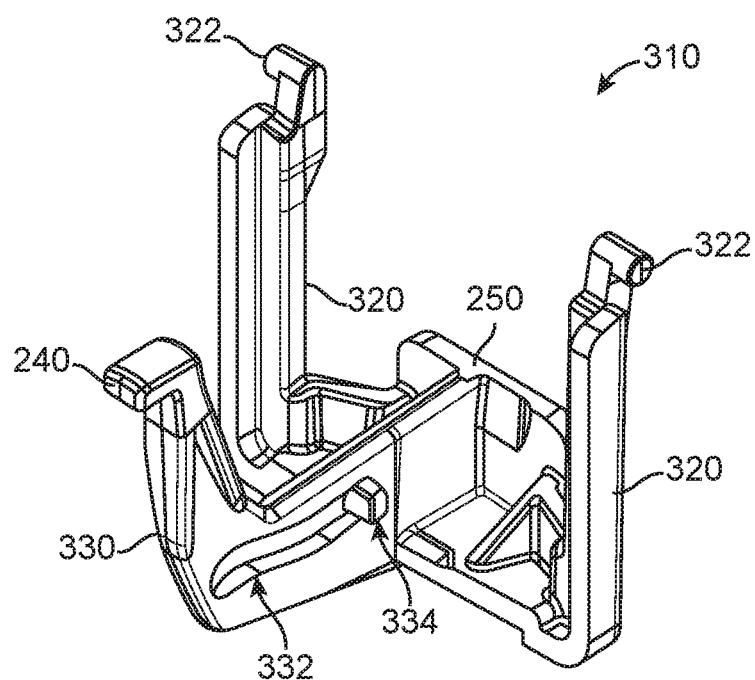

FIGS. 4A, 4B, and 4C respectively show front, side, and perspective views of an implementation of release lever 310 that can be used in release mechanism 300 of FIG. 3B. Release lever 310 may be a one-piece or monolithic structure and may be molded from a plastic or other sufficiently durable material. The release lever implementation of FIGS. 4A, 4B, and 4C includes guide channel 332 and a guide pin 334 on lifter arm 330 to allow interconnection of a pair of identical release levers 310. That is, to reduce parts and save manufacturing cost, identical release levers are used for each side, and the release levers are configured to work together in this hermaphroditic configuration. In particular, in assembling release mechanism 300 of FIG. 3B, guide pin 334 on the lifter arm 330 of one release lever 310 may be inserted into the guide channel 332 on the lifter arm 330 of the other release lever 310. Guide channel 332 may be arc-shaped to accommodate or guide rotations of both release levers 310 about their respective pivots 322. One of the advantages of the pin-in-slot configuration that is that guide channels 332 control the movement of pins 334, and so both release levers 310 are forced to move symmetrically. Thus, both tabs 240 may push upward on the sterile adapter retention features with the same displacement, and the instrument stays level relative to the sterile adapter and does not get cocked to one side when the tabs 240 push upward. Having two linked release levers 310 on opposite sides of the instrument also means that the force applied to one lever 310 is counteracted in the other 310, and user activation of release mechanism 300 does not produce a net force that might otherwise push the instrument left or right.

Lifter arm 330 on a release lever 310 extends from an off center location on release button 250 to position guide channel 332 and pin 334 for connection to the lifter arm 330 of an identical release lever 310. In some implementations, a spring may be inserted in a cavity formed by adjacent guide channels 332 to push guide pins 334 apart when no external pressure is applied to buttons 250.

A user can operate or activate release mechanism 300 of FIGS. 3A and 3B by grasping a backend 116 and depressing both buttons 250 simultaneously. Depressing buttons 250 causes both release levers 310 to rotate about their individual axes defined by the connection of pivots 322 to base plate 230 and guide pins 334 in channels 332, and the rotations of release levers 310 lift push tabs 240 relative to base plate 230.

The implementation of release lever 310 of FIGS. 4A, 4B, and 4C when assembled into the release mechanism 300 of FIGS. 3A and 3B has several advantageous features. In particular, pivot arms 320 may provide a long radius for rotation of button 250 about pivots 322 so that button 250 moves in a substantially linear direction when depressed. Further, the moment or radius of rotation of push tab 240 about pivot 322 may be roughly equal to moment or radius of rotation of button 250 about pivot 322, so that the force a user applies on button 250 may be about the same as the force that push tab 240 exerts on the retention plate when release mechanism 300 is activated. Further, the one-piece structure of release levers 310 and the hermaphroditic engagement of release levers 310 in release mechanism 300 allow both release levers 310 to be identical parts, which may reduce the part count and cost of a medical instrument. Release levers 310 can also extend across an instrument backend and wrap around backend mechanical systems such as the input spindles and cables shown in FIG. 3A. Release mechanism 300 may, therefore, be installed in an instrument backend after all cabling and centrally located mechanical systems are assembled, which simplifies the instrument assembly process because release mechanism 300 does not interfere with assembly of other backend mechanical systems.

Figure 5A:
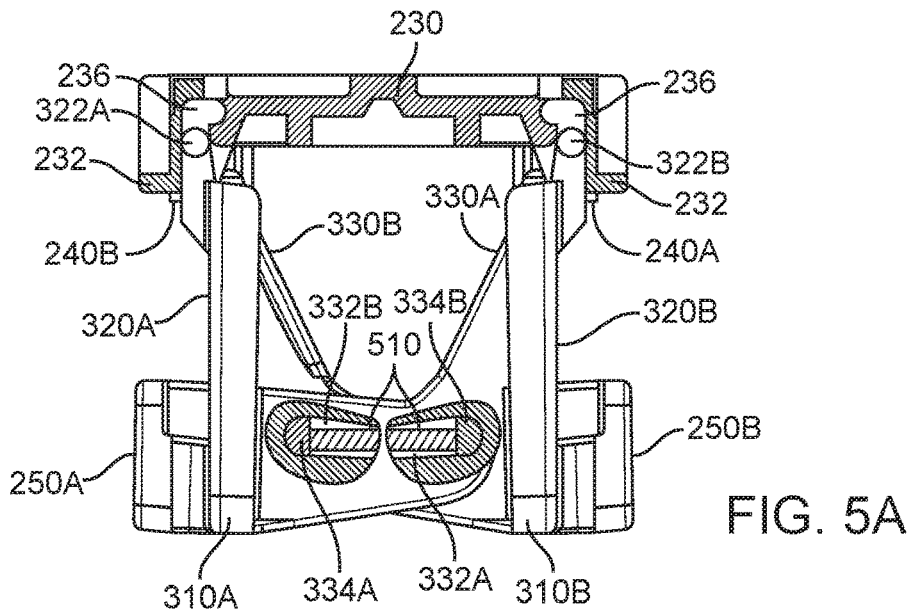
FIGS. 5A, 5B, and 5C are cross-sectional views illustrating installation of a release mechanism in a medical instrument.
Figure 5B:
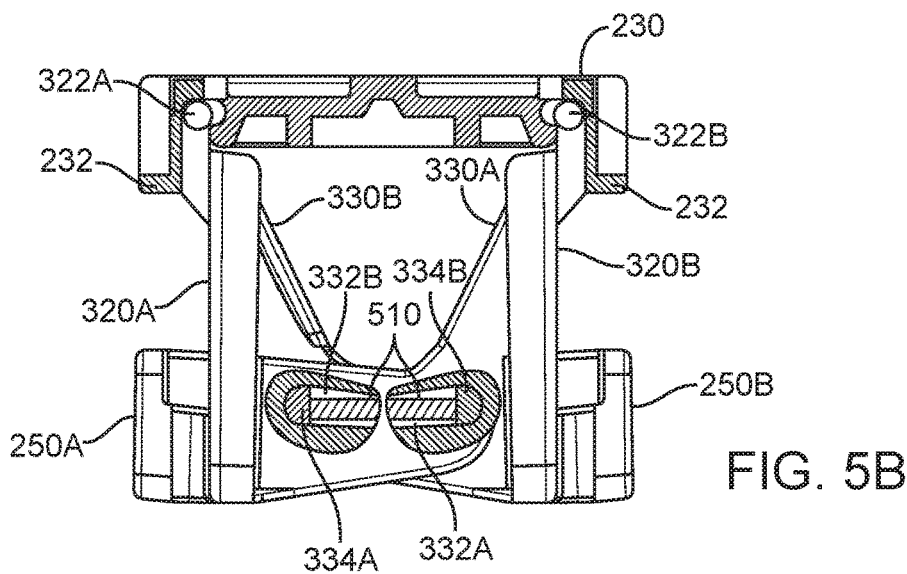
Figure 5C:
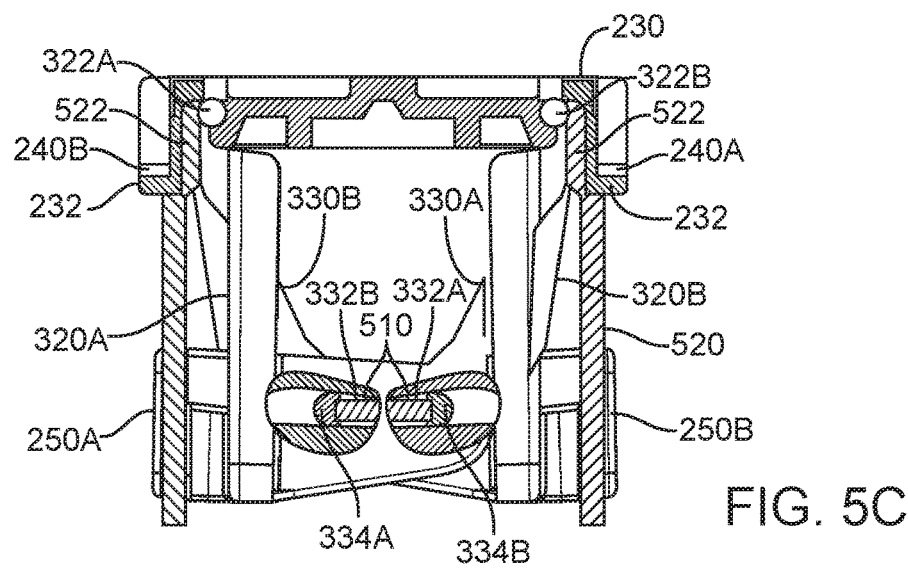

FIGS. 5A, 5B, and 5C illustrate a process of assembling a pair of identical release levers 310A and 310B in a base plate 230 of an instrument backend to form one implementation of an instrument release mechanism 300. Each release lever 310A or 310B may have a one-piece molded construction including two pivot arms 320A or 320B and a lifter arm 330A or 330B as described above. Release levers 310A and 310B may be engaged with each other before being engaged with base plate 230. In particular, a guide pin 334A of release lever 310A may be inserted in a guide channel 332B of release lever 310B, and a guide pin 334B of release lever 310B may be inserted in a guide channel 332A of release lever 310A. A spring 510 may be installed between guide pins 334A and 334B in a cavity formed by guide channels 332A and 332B and may improve the look and feel of release buttons 250A and 250B in the assembled release mechanism 300.

Each guide channel 332A and 332B may extend beyond the range of motion that guide pins 334B and 334A have for normal use of release mechanism 300. In particular, an assembly process may initially separate pivots 322A and 322B by a greater distance than required for normal use. The wider separation allows pivots 322A and 322B to be inserted into L-shaped slots 236 in base plate 230 as shown in FIG. 5A. Pivots 322A and 322B may then be slid up into slots 236 as shown in FIG. 5B before buttons 250A and 250B, and pivots 322A and 322B shift inward for use as shown in FIG. 5C. Accordingly, guide channels 332A and 332B may have extensions that can accommodate the greater separation initially needed between guide pins 334B and 334A during assembly of release mechanism 300.

Figure 5D:
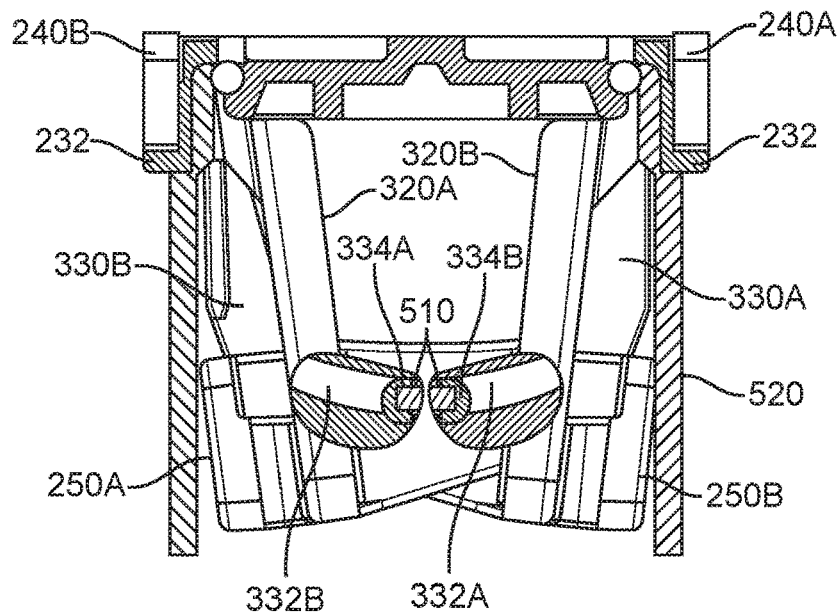
FIG. 5D shows a cross-sectional view illustrating the effect of a user depressing or activating a release mechanism in accordance with the implementation of FIGS. 5A, 5B, and 5C.

FIG. 5C also illustrates a housing 520 for the instrument backend that encloses the mechanics of the backend including release mechanism 300. Housing 520 may include tabs 522 that fit into the L-shaped slots in base plate 230 and help to capture the release lever pivots 322A and 322B in their working positions. Housing 520 also captures release buttons 250A and 250B at the proper separation so that push tabs 240A and 240B are substantially aligned with rails 232. The bottom cutaways in FIG. 5C show how spring 510 compresses to fit between guide pins 334A and 334B in the assembled position, which loads spring 510 to push the release buttons 250A and 250B apart. FIG. 5D illustrates how pushing release buttons 250A and 250B inward rotates release levers 310A and 310B about respective pivots 322A and 322B, raising push tabs 240A and 240B above rails 232 so that push tabs 240A and 240B can push on an ISA or other docking structure.

Figure 6A:
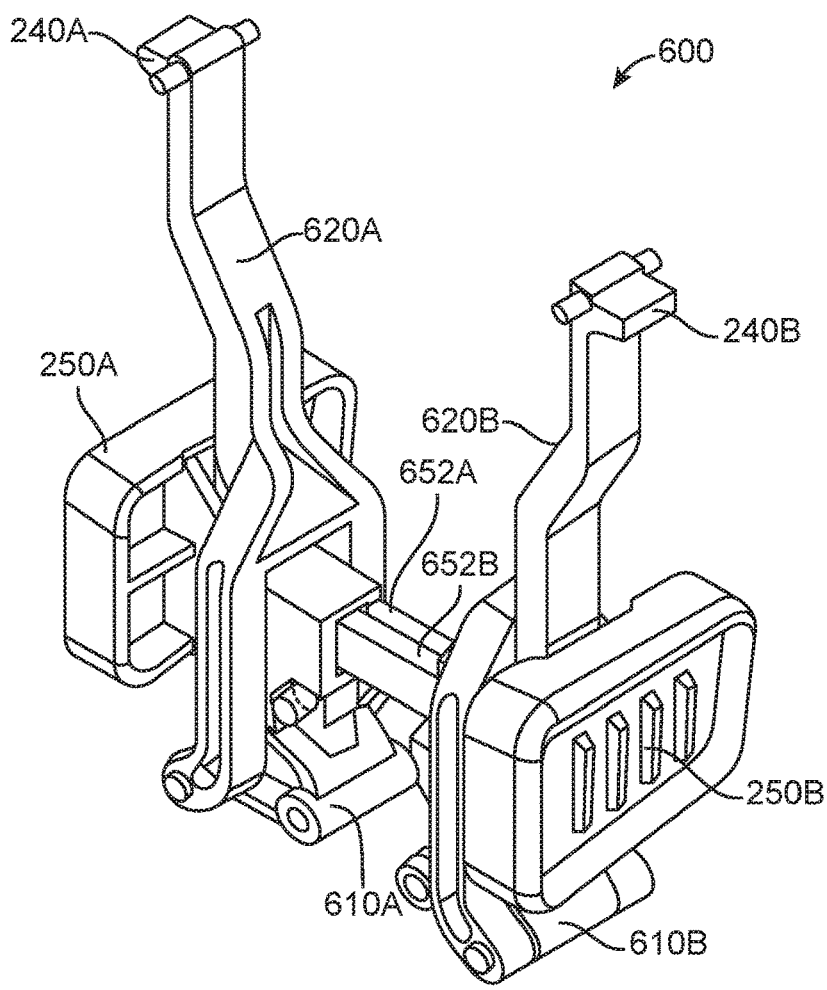
FIG. 6A shows a perspective view of a release mechanism in accordance with an implementation employing multi-piece release levers.
Figure 6B:
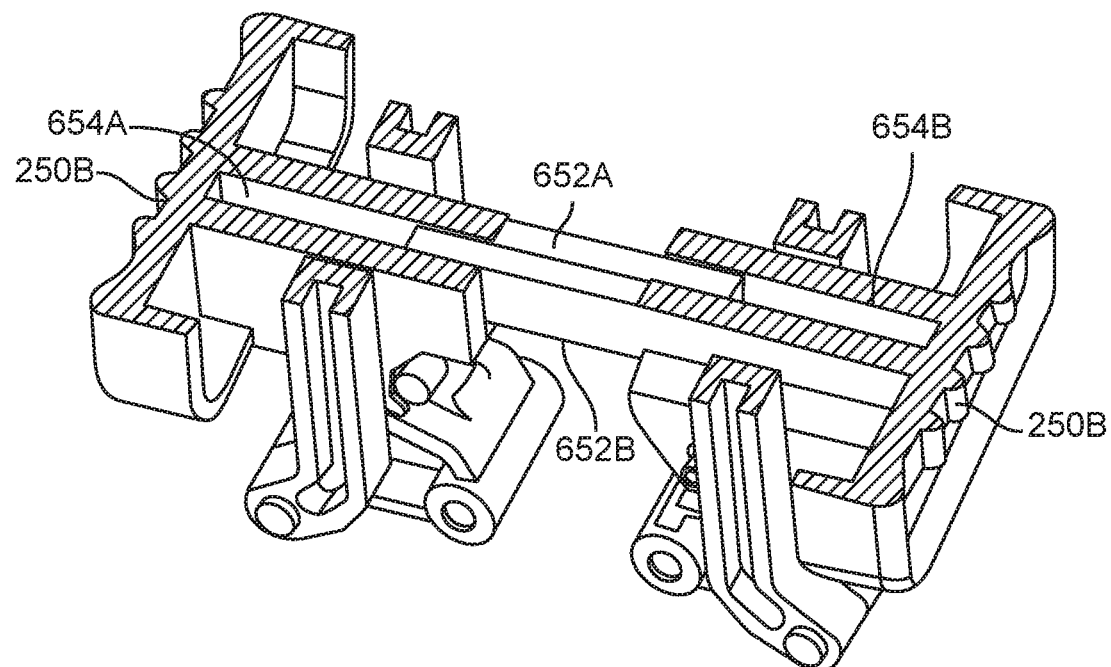
FIG. 6B is a cutaway view illustrating the interconnection of release buttons on opposite sides of a medical instrument using the release mechanism of FIG. 6A.

FIG. 6A shows a release mechanism 600 in accordance with an implementation that positions push tab 240A on the same side as release button 250A on an instrument backend, and likewise push tab 240B is on the same side as release button 250B on the instrument backend. In release mechanism 600, release buttons 250A and 250B are interconnected using alignment features that limit buttons 250A and 250B to moving linearly toward or away from each other. For example, FIG. 6B shows an implementation in which slides 652A and 652B on release buttons 250A and 250B fit into slots 654B and 654A in the opposite release buttons 250B and 250A, so that buttons 250A and 250B can only move relative to each other along a length axis of slides 652A and 652B. As described above, the release mechanism assemblies for each side are identical and are configured to work together.

Figure 6C:
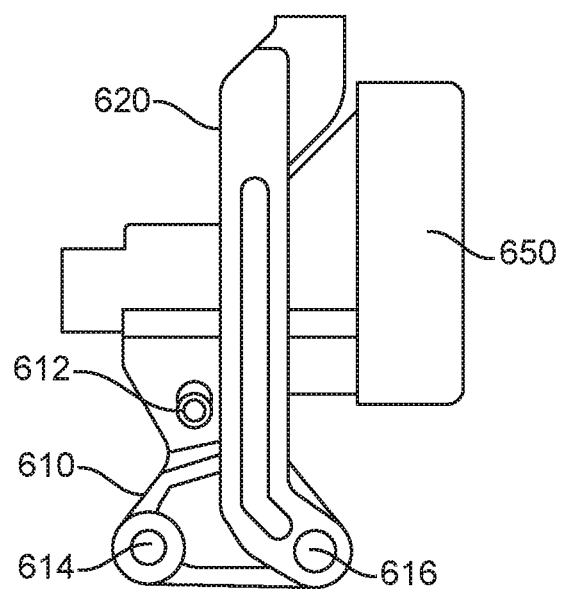
FIG. 6C is a side view illustrating the connection an release button to a link and a push rod that form an implementation of a multi-piece release lever.

Each release button 250A or 250B in release mechanism 600 of FIG. 6A further couples to a three-pivot link 610A or 610B. FIG. 6C, for example, shows a release button 650, which may be identical to button 250A or 250B, having a slot and pin coupling 612 to a three-pivot link 610, which may be identical to link 610A or 610B of FIG. 6A. A second pivot 614 of link 610 may be fixed on a chassis of a backend of an instrument containing the release mechanism 600, and a third pivot 616 of link 610 couples link 610 to a push rod 620. During use of release mechanism 600, pushing on release button 650 rotates link 610 and thereby pushes push rod 620 upward. Accordingly, in release mechanism 600 of FIG. 6A, pushing on button 250A or 250B rotates the connected link 610A or 610B and moves push rod 620A or 620B in a generally upward direction. Push tabs 240A and 240B may have guide features that restrict the movement of tabs 240A and 240B to desired directions, e.g., up and down. Thus as shown, each assembly of button 250, slides 652, link 610, and push rod 620 functions as a release element of the release assembly.

Figure 6D:
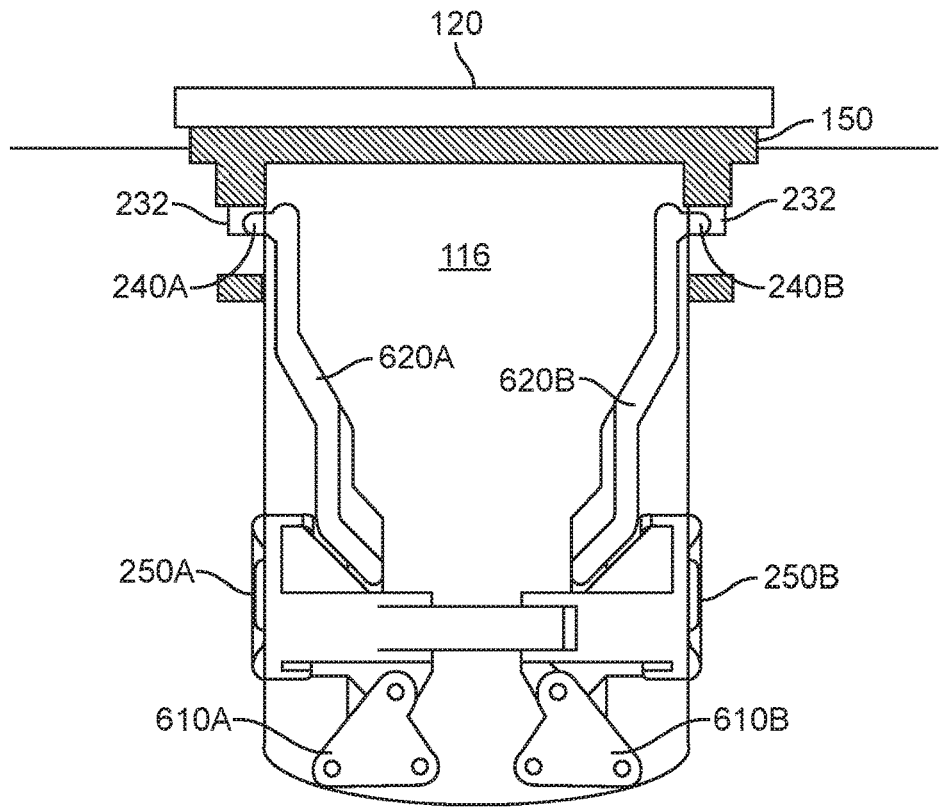
FIG. 6D shows an instrument containing the release mechanism of FIG. 6A when the instrument is engaged with an instrument sterile adapter and a docking port of a robot.
Figure 6E:
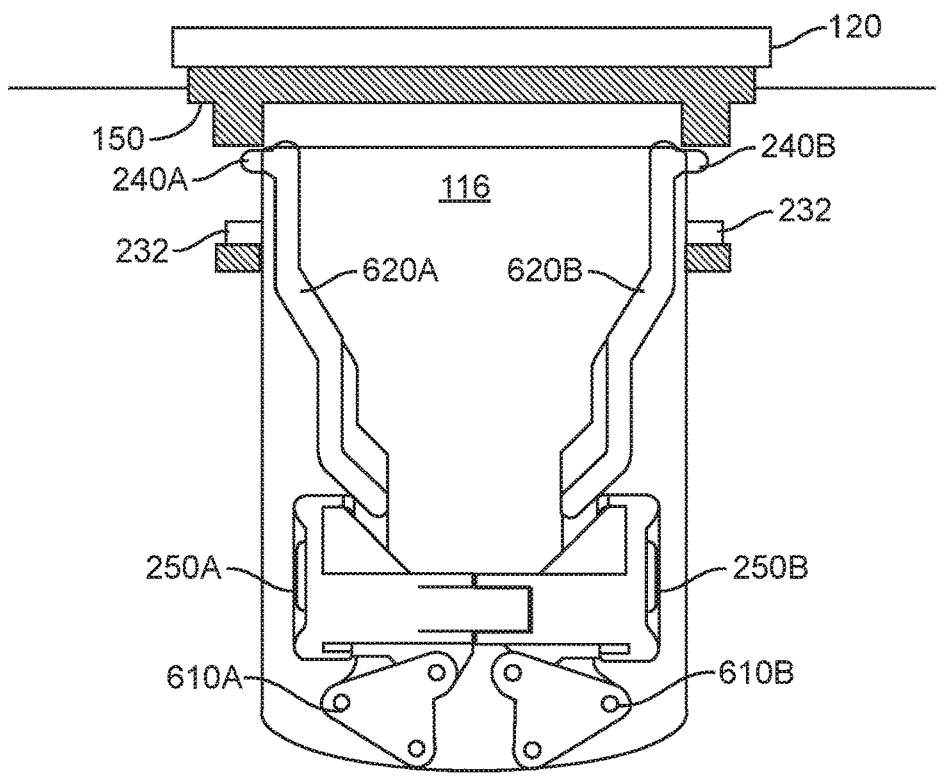
FIG. 6E shows an instrument containing the release mechanism of FIG. 6A when the release mechanism is activated.

FIG. 6D shows an implementation of an instrument backend 116 containing release mechanism 600 of FIG. 6A when instrument backend 116 is engaged with a docking port 120 via an ISA 150. In the engaged configuration as shown in FIG. 6D, push tabs 240 may be aligned with side rails 232 on the housing of backend 116. As described above with reference to FIG. 1C, backend 116 and ISA 150 may have complementary projections and notches that fit together and prevent backend 116 from being slid out of ISA 150 while the projections and notches are engaged. When a user presses release both buttons 250A and 250B as shown in FIG. 6E, resulting rotations of links 610A and 610B move push rods 620A and 620B upward, so that push tabs 240A and 240B push on ISA 150, which can disengage projections and notches on backend 116 and ISA 150. Pushing release buttons 250A and 250B may thus release backend 116 from ISA 150, while ISA 150 and docking port 120 remain engaged.

Although particular implementations have been disclosed, these implementations are only examples and should not be taken as limitations. Various adaptations and combinations of features of the implementations disclosed are within the scope of the following claims.

What is claimed is:

1. A medical instrument comprising:
   a backend including a docking feature shaped to engage a docking structure;
   a first release lever coupled to the backend and including a first activation feature on a first side of the backend and a first push tab extending from a second side of the backend, the second side being opposite to the first side; and
   a second release lever coupled to the backend and including a second activation feature on the second side of the backend and a second push tab extending from the first side of the backend;
   wherein a movement of the first and second activation features moves the first and second push tabs from being aligned with the docking feature to pushing on a portion of the docking structure to separate the portion of the docking structure and the backend.

2. The medical instrument of claim 1, wherein the docking structure comprises an instrument sterile adapter that is part of a sterile barrier separating the medical instrument from a manipulator docking port.

3. The medical instrument of claim 1, wherein the docking feature comprises:
a rail shaped to slide into the docking structure; and
a lock feature shaped to engage the docking structure and prevent the medical instrument from being slid out of the docking structure when engaged.

4. The medical instrument of claim 3, wherein the first and second push tabs pushing on the docking structure disengages the lock feature from the docking structure, thereby allowing the medical instrument to be slid out of the docking structure.

5. The medical instrument of claim 1, wherein:
the first activation feature comprises a first button;
the second activation feature comprises a second button; and
the first and second buttons are positioned so that a user can simultaneously depress the first and second buttons by grasping the backend.

6. The medical instrument of claim 1, wherein the first release lever comprises a monolithic structure including:
the first activation feature;
the first push tab;
a first pivot arm extending from the first activation feature to a first pivot that attaches to the backend on the first side; and
a lifter arm extending from the first activation feature to the second side of the backend, the first push tab extending from the lifter arm.

7. The medical instrument of claim 6, wherein the monolithic structure further includes a second pivot arm extending from the first activation feature to a second pivot that attaches to the backend on the first side.

8. The medical instrument of claim 1, wherein:
the first release lever comprises a first pin and a first guide channel;
the second release lever comprises a second pin and a second guide channel;
the first pin is in the second guide channel; and
the second pin is in the first guide channel.

9. The medical instrument of claim 8, wherein shapes of the first and second guide channels control movement of the first and second pins and force the first and second release levers to move symmetrically during movement of the first and second activation features.

10. The medical instrument of claim 8, wherein interaction of the first and second guide channels with the first and second pins and causes a reactive force in response to an activation force applied to one of the first and second release levers, the reactive force counteracting the activation force so that a net force does not push the medical instrument perpendicular to a direction in which the first and second push tabs move.

11. The medical instrument of claim 1, wherein the first release lever and the second release lever are identical.

12. A medical instrument comprising:
a backend including a docking feature shaped to engage a docking structure; and
a release mechanism including:
a first release element including a first activation feature on a first side of the backend,
a second release element including a second activation feature on a second side of the backend opposite the first side,
a first push tab extending from the first side of the backend, and
a second push tab extending from the second side of the backend,
wherein the first release element and the second release element are coupled together to limit a movement of the first and second activation features, and
wherein the movement of the first and second activation features moves the first and second push tabs from being aligned with the docking feature to pushing on a portion of the docking structure to separate the portion of the docking structure and the backend.

13. The medical instrument of claim 12, further comprising an actuation mechanism in the backend between the first release element and the docking structure.

14. The medical instrument of claim 12, wherein the first push tab is part of the second release element and the second push tab is part of the first release element.

15. The medical instrument of claim 12, wherein the first push tab is part of the first release element and the second push tab is part of the second release element.

16. The medical instrument of claim 15, wherein the first release element comprises:
a first link having a first pivot coupled to the backend and a second pivot coupled to the first activation feature so that moving the first activation feature rotates the first link about the first pivot; and
a first push rod coupled to a third pivot of the first link, wherein the first push tab extends from the first push rod.

17. The medical instrument of claim 16, wherein the second release element comprises:
a second link having a first pivot coupled to the backend and a second pivot coupled to the second activation feature so that moving the second activation feature rotates the second link about the first pivot of the second link; and
a second push rod coupled to a third pivot of the second link, wherein the second push tab extends from the second push rod.

18. The medical instrument of claim 17, wherein the first release element and the second release element are coupled together to limit the first and second activation features to moving linearly toward or away from each other.

19. The medical instrument of claim 12, wherein the first activation feature and the second push tab are directly coupled by a lever comprising a pivot arm and a lifting arm.

20. The medical instrument of claim 12, wherein the first release element and the second release element each have the same configuration.

* * * * *